United States Patent [19]

Ono et al.

[11] Patent Number: 4,587,333

[45] Date of Patent: May 6, 1986

[54] CEPHALOSPORINS AND THEIR PRODUCTION

[75] Inventors: Hideo Ono, Kobe; Yukimasa Nozaki, Ikeda; Setsuo Harada, Kawanishi, all of Japan

[73] Assignee: Takeda Chemical Industries, Ltd., Osaka, Japan

[21] Appl. No.: 651,037

[22] Filed: Sep. 14, 1984

[30] Foreign Application Priority Data

Sep. 20, 1983 [JP] Japan ................. 58-174897

[51] Int. Cl.$^4$ ................. C07D 501/08; C07D 501/28; A61K 31/545
[52] U.S. Cl. ....................... 544/21; 544/20; 544/30; 514/201; 514/209; 435/253
[58] Field of Search ............... 544/21, 30; 514/201, 514/209

[56] References Cited

FOREIGN PATENT DOCUMENTS 2107307 4/1983 United Kingdom .

OTHER PUBLICATIONS

The Journal of Antibiotics, vol. 37, No. 7, pp. 773–780, Jul. 1984.

Primary Examiner—Donald G. Daus
Assistant Examiner—G. Hendricks
Attorney, Agent, or Firm—Wenderoth, Lind & Ponack

[57] ABSTRACT

A compound of the formula:

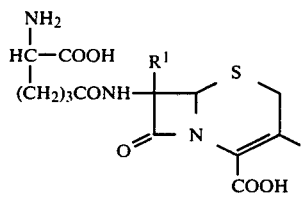

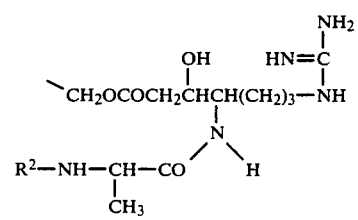

wherein $R^1$ stands for hydrogen or formylamino, $R^2$ stands for hydrogen, alanyl or alanyl-alanyl, or its salt, which can be produced by cultivating a microorganism belonging to the genus Lysobacter, is useful as a therapeutic agent against infectious disease caused by bacteria.

8 Claims, 12 Drawing Figures

CEPHALOSPORINS AND THEIR PRODUCTION

The present invention relates to novel cephalosporins and their production.

The present inventors, with a specific view to the search for novel antibiotics, isolated a large number of microorganisms from soils or plants and performed screenings for identifying the antibiotics which the microorganisms produce. As a result, it was found that a certain microorganism is able to produce novel antibiotic, that said microorganism belongs to a novel species of the genus Lysobacter, and that cultivation of said microorganism in a suitable culture medium results in accumulation in the nutrient medium of the antibiotic which exhibits antimicrobial activity against gram-positive and negative bacteria including β-lactamase producing strain. The inventors isolated this antibiotic, ascertained from its physico-chemical and biological properties that said antibiotic is a novel antibiotic, and named this Antibiotic TAN-547. TAN-547 is composed of at least six components, which the present inventors named as TAN-547 A, B, C, D, E and F.

The present inventors conducted further research based on these findings, and have completed the present invention.

The present invention relates to (1) a compound of the formula:

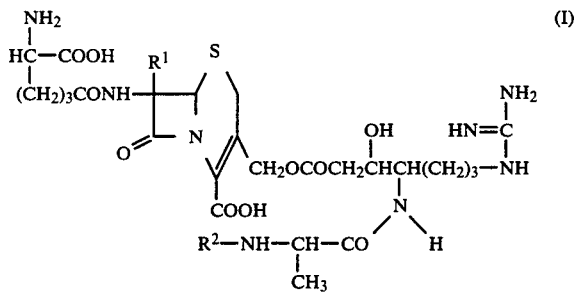

wherein $R^1$ stands for hydrogen or formylamino, and $R^2$ stands for hydrogen, alanyl or alanyl-alanyl or its salt thereof, and (2) a method for producing the compound (I) or a salt thereof, which comprises cultivating in a culture medium a microorganism belonging to the genus Lysobacter which is capable of elaborating a compound of the formula (I) to have the compound (I) accumulated in the culture broth and harvesting the compound (I).

In the formula, alanyl represents

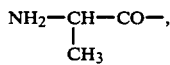

alanyl-alanyl represents

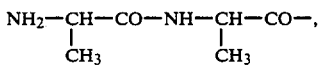

formylamino represents

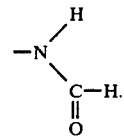

In the present specification, the compounds shown by the formula (I) are named as follows:

| Antibiotic | $-R^1$ | $R^2-$ |
|---|---|---|
| TAN-547 A | $-NH-CHO$ | $H-$ |
| TAN-547 B | $-NH-CHO$ | alanyl- |
| TAN-547 C | $-NH-CHO$ | alanyl-alanyl- |
| TAN-547 D | $-H$ | $H-$ |
| TAN-547 E | $-H$ | alanyl- |
| TAN-547 F | $-H$ | alanyl-alanyl- |

In this specification, the term "Antibiotic TAN-547" or the abridged term "TAN-547" will be sometimes used in order to refer to the individual Antibiotic TAN-547 A, B, C, D, E or F, or a mixture containing at least two of them.

Throughout this specification, furthermore, the microorganism which is capable of producing one kind or more kinds of Antibiotic TAN-547 will be sometimes referred to as "Antibiotic TAN-547 producing strain".

As the Antibiotic TAN-547 producing strain which is used in this invention, any and all microorganisms may be employable, only if they belong to the genus Lysobacter and are capable of producing Antibiotic TAN-547. Their examples include a new species of microorganism, *Lysobacter lactamgenus*. As specific examples thereof, there may be mentioned *Lysobacter lactamgenus* YK-90 (hereinafter referred to in some instances briefly as "Strain YK-90") which was isolated from a soil sample collected at Niimi City, Okayama Prefecture, Japan.

The microbiological characteristics of Strain YK-90 are described in the following:

(a) Morphology:

Observation after the cultivation on a nutrient-agar slant at 24° C. for 5 days reveals that the cells are in the form of rod having a diameter of 0.7 to 0.9 μm and a length of 1.0 to 3.5 μm or sometimes in the form of elongated rod having a length of 6.5 to 8.0 μm; and that the microorganism, without flagella observed, exhibits gliding motility, forms no spore, and is gram-negative but not acid-fast.

(b) The growth characteristics on various media:

Observation was made during the cultivation at 24° C. over the period of 1 to 14 days.

(1) Nutrient-agar plate culture: Opaque, pale yellow and circular colonies with convex surface and entire margin. No diffusive pigment produced.

(2) Nutrient-agar slant culture: Moderate, spreading growth. Opaque and pale yellow.

(3) Nutrient liquid culture: Thin, turbid growth, with pellicle formed. No sediment formed.

(4) Nutrient-gelatin stab culture: Good growth on the surface and growth observed on the middle and deep parts. Stratiform and saccate liquefaction, with strong liquefaction activity.

(5) Litmus milk: Weak reduction ability. Strong peptonization activity, but no coagulation observed.

(c) Physiological properties:

(1) Reduction of nitrates: —

(2) Denitrification reaction: —

(3) MR (methyl red) test: —
(4) VP (Voges-Proskauer) test: —
(5) Production of indole: —
(6) Production of hydrogen sulfide (TSI agar and lead-acetate-paper): —

TSI agar: 4 g of meat extract, 15 g of peptone, 10 g of lactose, 10 g of white sugar, 1 g of glucose, 5 g of sodium chloride, 0.08 g of sodium thiosulfate, 0.4 g of sodium sulfite, 0.2 g of ferrous sulfate, 0.02 g of phenol red, 15 g of agar, 1000 ml of distilled water, pH 7.4.

(7) Hydrolysis of starch: —
(8) Utilization of citric acid (Koser's, Christensen's and Simmons' culture media): +
(9) Utilization of nitrogen source
 (I) Potassium nitrate: —
 (II) Ammonium sulfate: +
 (III) Sodium glutamate: +
(10) Production of pigments (King A and B and mannitol-yeat extract-agar culture media): No production of diffusive pigment observed.

King A culture medium: 10 g of glycerol, 20 g of peptone, 1.4 g of magnesium chloride, 10 g of ammonium sulfate, 15 g of agar, 1000 ml of distilled water, pH 7.2.

King B culture medium: 10 g of glycerol, 20 g of peptone, 1.5 g of potassium hydrogenphosphate, 1.5 g of magnesium sulfate, 15 g of agar, pH 7.2.

(11) Urease: —
(12) Oxidase: +
(13) Catalase: ±(quasipositive)
(14) Ranges for the growth
 (I) pH: The microorganism grows at pH 5.4 to 7.6. The optimum pH is 5.6 to 6.6.
 (II) Temperature: The microorganism grows at 10 to 30° C. The optimum temperature is 15 to 27° C.
(15) Oxygen demand: Aerobic to faculatively anaerobic.
(16) O-F (Oxidative-fermentative) test (Hugh.Leifson method): Not degradative
(17) Production of acid and gas from sugars:

|  | Acid Peptone-water | Gas Peptone-water | Utilization (Davis medium) |
|---|---|---|---|
| L-Arabinose | — | — | — |
| D-Xylose | — | — | — |
| D-Glucose | — | — | + |
| D-Mannose | — | — | + |
| D-Fructose | — | — | — |
| D-Galactose | — | — | — |
| Maltose | — | — | + |
| Sucrose | — | — | — |
| Lactose | — | — | + |
| Trehalose | — | — | + |
| D-Sorbitol | — | — | ± |
| D-Mannitol | — | — | — |
| Inositol | — | — | — |
| Glycerin | — | — | — |
| Starch | — | — | ± |

(18) GC guanine+cytosine) content in DNA: 75.8±1.5%
(19) The ability to form mycrocysts: —
(20) The ability to decompose carboxymethylcellulose: +
(21) The ability to decompose colloidal chitin: +

When Strain YK-90 is compared with the species as described in Bergey's Mannual of Determinative Bacteriology, 8th edition, and in International Journal of Systematic Bacteriology, 30, 225–420 (1980) and 32, 146–149 (1982), it is reasonable that Strain YK-90 be deemed as belonging to the genus Lysobacter, because the strain is a flagellum-free, yellow gram-negative rod exhibiting motility by means of gliding, is aerobic, has a high GC content in DNA and is devoid of the ability to form microcysts. Consequently, strain YK-90 was compared with the known species of the genus Lysobacter. As the known species of the genus Lysobacter, there are known only four species and one subspecies described in International Journal of Systematic Bacteriology, 28, 367–393 (1978). Comparison of the characteristics of Strain YK-90 with the descriptions of these five species (45 strains are described in the above literature) led us to inability to find any known strain of microorganisms which shared all of the below-described characteristics with Strain YK-90; namely in that (1) the oxidative-fermentative test is not degradative, (2) production of acid and gas from sucrose and lactose is not observed, (3) production of soluble pigment is not observed, (4) the ability to hydrolyze starch is lacking, and (5) utilization of nitrates is absent.

Therefore, we identified Strain YK-90 as a strain belonging to the novel species of microorganism, and named the said novel species Lysobacter lactamgenus.

The above Lysobacter lactamgenus YK-90, has been deposited as of 14th September, 1983 at the Institute for Fermentation, Osaka (IFO), Japan under the deposit number of IFO 14288. This microorganism has also been deposited as of 19th September, 1983 at the Fermentation Research Institute, Agency of Industrial Science and Technology, Ministry of International Trade and Industry (FRI), Japan under the deposit number of FERM P-7247, and the deposit has been converted to a deposit under the Budapest Treaty, and has been stored at FRI under the accession number of FERM BP-575.

The microorganism of the genus Lysobacter which is used in the present invention is generally liable to vary its characteristics, and can be easily caused to undergo mutation by artificial mutation means using for example ultraviolet light, X-rays and chemical agents (e.g., nitrosoguanidine, ethylmethanesulfonic acid, etc.). Any of such mutants can also be used in the present invention insofar as they are capable of producing the compound (I) that the present invention aims at.

In the cultivation of the compound (I) producing strain, as the carbon source, use is suitably made of carbon sources which are assimilatable to the strain, such as glucose, maltose, spent molasses, fats and oils (e.g., soybean oil, olive oil, etc.) and organic acids (e.g., citric acid, succinic acid, gluconic acid, etc.). As the nitrogen source, organic nitrogen compounds and inorganic nitrogen compounds, such as soybean meal, cottonseed meal, corn steep liquor, dried yeast, yeast extract, meat extract, peptone urea, ammonium sulfate, ammonium nitrate, ammonium chloride and ammonium phosphate, can be utilized. As the inorganic salt, inorganic salts which are normally required for the cultivation of microorganisms, such as sodium chloride, potassium chloride, calcium carbonate, magnesium sulfate, monopotassium phosphate and disodium phosphate, are used solely or in suitable combination. If sulfur compounds which the compound (I) producing strain of the genus Lysobacter can assimilate, such as inorganic sulfur compounds exemplified by sulfates (e.g., ammonium sulfate, etc.). thiosulfates (e.g., ammonium thio-sulfate, etc.) and sulfites (e.g., ammonium sulfite, etc.), organic sulfur compounds exemplified by sulfur-containing amino acids (e.g., cystine, cysteine, L-thiazolidine-4- carboxylic acid, etc.), hypotaurine and sulfur-containing peptides (e.g., glutathion, etc.) or mixtures thereof, are added to the culture medium, the production amount of the objective compound may be sometimes increased.

Furthermore, heavy metals such as ferrous sulfate and copper sulfate, vitamins such as vitamin $B_1$ and biotin, and so forth are added, if desired. In addition, antifoams such as silicone oil and polyalkylene glycol ether and surface active agents may be added. Other organic and inorganic materials which can support the growth of the microorganism and promote the production of the compound (I) may be suitably added.

With reference to the cultural method, the cultivation may be conducted in the same manner as the processes for the production of common antibiotics, and may be by means of the solid or liquid cultural method. In the case of liquid culture, any of stationary culture, submerged culture, shake culture, aerated culture, etc. may be conducted, though submerged aerobic culture is particularly preferable. The temperature of incubation is preferably in the range of about 10° C. to 30° C., and the cultivation is carried out over the pH range of about 4 to 8 for 8 to 168 hours, preferably for 24 to 144 hours.

For recovering the objective compound (I), the conventional isolation means employed in the harvesting of metabolites produced by a microorganism from the microbial culture is suitably utilized. Since the compound (I) is provided with properties of aqueous basic substance (the antibiotic, which contains weakly acid functional groups too, is a basic substance as the whole molecule) and is contained predominantly in the filtrate of the cultured broth, for example, a filter aid is in the first place added to the cultured broth and microbial cells are removed by filtration or centrifugation; the resulting filtrate is contacted with a suitable support to adsorb the active ingredient in the filtrate, and the active ingredient is desorbed with a suitable solvent. Such means of isolation and harvesting is advantageously utilized. As the support or adsorbent for chromatography, advantageous use is made of those utilizing the difference in adsorptive power of compounds such as activated carbon, silica gel, powdered cellulose and adsorptive resins, those taking advantage of the difference in functional group of compounds such as cationic exchange resins, cationic exchange cellulose and cationic exchange Sephadex, and those utilizing the difference in molecular weight of compounds such as Sephadex products. In order to elute the objective compound from these supports, for example, aqueous solutions of water soluble organic solvents such as aqueous acetone and aqueous alcohols, or aqueous solutions containing acid, alkali, buffer or inorganic or organic salts are used in suitable combinations, which vary depending upon the type and nature of supports.

Also, the crude product containing the antibiotic as obtained by these chromatographic procedures is subjected to preparative high-performance liquid chromatography (HPLC) for separation to yield the purified product.

In more particular, when a cationic exchange resin such as Dowex-50W (produced by Dow Chemical Co., U.S.A.), Amberlite IR-120 and 200 (produced by Rohm & Haas Co., U.S.A.) and Diaion SK 116 (produced by Mitsubishi Chemical industries, Ltd., Japan) is employed as a support, the antimicrobial substance in the filtrate is adsorbed on the support, and then eluted with an aqueous solution containing salts, acids or buffer, etc.

Alternatively, the antibiotic can be adsorbed on such a support as cationic exchange, molecular sieve resin, for example CM-Sephadex (Pharmacia Fine Chemicals Co., Sweden), and eluted with an aqueous solution containing salts or acids or buffer, etc. In order to remove salts, coloring materials, etc. in these eluates, activated carbon for chromatographic use (produced by Takeda Chemical Industries, Ltd., Japan) or adsorptive resins such as Diaion HP-20 (produced by Mitsubishi Chemical Industries, Ltd., Japan) and Amberlite XAD-II(produced by Rohm & Haas Co., U.S.A.) are advantageously employed. The eluates fractionated are powdered by subjecting to steps such as concentration and lyophilization. For the purpose of further purification when the purity of the powder thus obtained is low, preparative HPLC method is advantageously used. As the support which is useful in the method, there may be mentioned, for example, TSK Gel (produced by Toyo Soda Mfg. Co., Japan), YMC Gel (produced by Yamamura Chemical Research Institute, Japan), etc., and as the mobile phase, use is made of mixtures of methanol or acetonitrile, etc. with aqueous solutions containing inorganic salts or buffer, etc. The compound (I) is isolated in the form of a pharmaceutically acceptable salt with mineral acids such as hydrochloric acid, sulfuric acid and phosphoric acid or organic acids such as formic acid, acetic acid and oxalic acid.

The physico-chemical properties of Antibiotic TAN-547.dihydrochloride obtained in Examples 1 and 2 which appear hereinafter are shown below.

(i) TAN-547A.dihydrochloride:
 (1) Appearance: White powder.
 (2) Specific rotation: $[\alpha]_D^{25} + 71.8° \pm 20°$ (c=0.50, in water).
 (3) Molecular weight: SIMS method, $(M+H)^+ 688$.
 (4) Molecular formula: $C_{26}H_{41}N_9O_{11}S \cdot 2HCl \cdot (3H_2O)$.

| (5) Elemental analysis (%): | Found*1 | Calcd.*2 |
|---|---|---|
| | C, 38.29 ± 2.0 | C, 38.33 |
| | H, 6.48 ± 1.0 | H, 6.06 |
| | N, 15.11 ± 1.5 | N, 15.47 |
| | | O, 27.49 |
| | S, 4.12 ± 1.0 | S, 3.94 |
| | Cl, 8.71 ± 1.5 | Cl, 8.70 |

*1the sample was dried over diphosphorus pentoxide for 15 hours at room temperature under reduced pressure.
*2the value is calculated as the sample contains 3 moles of water.

(6) Ultraviolet absorption (UV) spectrum: FIG. 1 $\lambda_{max}^{H_2O}$ 260±2 nm ($E_{1cm}^{1\%} = 117 \pm 20$).

(7) Circular dichromatic (CD) spectrum: $[\theta]_{228 \pm 2}^{H_2O} - 30900 \pm 5000$ and $[\theta]_{260 \pm 2}^{H_2O} + 29500 \pm 5000$ (−: negative (−) Cotton effect; +: positive (+) Cotton effect).

(80) Infrared absorption (IR) spectrum: Main wave number (cm$^{-1}$) in KBr tablet: FIG. 2 3420, 3250, 3080, 3000, 1775, 1730, 1670, 1510, 1450, 1400, 1260, 1165, 1060, 980, 860, 510.

(9) Nucleic magnetic resonance ($^{13}$C-NMR) spectrum: in D$_2$O, signals at 100 MHz are shown below (δppm). 179.84(s), 177.42(s), 176.05(s), 173.75(s), 171.12(s), 166.40(d), 162.16(s), 159.62(s), 134.86(s), 117.40(s), 79.64(s), 72.66(d), 67.16(t), 65.94(d), 57.34(d), 56.31(d), 52.03(d), 43.59(t), 41.23(t), 37.36(t), 32.80(t), 28.98(t), 28.60(t), 27.50(t), 23.50(t), 19.75(q). (s: singlet, d: doublet, t: triplet, q: quartet).

(10) Amino acid analysis: in 5.5N—HCl, 110° C., the sample was hydrolized for 15 hours. Alanine; 0.86 mole. α-amino-adipic acid; 0.94 mole.

(11) Thin layer chromatography (TLC): Spot film cellulose (Tokyo Chemical Industries, Ltd., Japan) Solvent system, acetonitrile: 3% ammonium sulfate (1:1), Rf=0.52.

(12) High performance liquid chromatography (HPLC): column, YMC pack A312 (Yamamura Chemical Research Institute), mobile phase, 2% methanol/0.01M phosphate buffer (pH 3.0), 2 ml/min. Rt=5.8(min) The following properties are in common among the components A, B and C (dihydrochloride).

(13) Solubility: Easily soluble: water, aqueous acetone, aqueous alcohol. Hardly soluble: dimethylsulfoxide, methanol, acetone, ethyl acetate.

(14) Color reaction: Positive: ninhydrine, Greig-Lieback, Sakaguchi reactions. Negative: Ehrlich, Barton reactions, potassium permanganate.

(15) Stability: Unstable in acidic and basic aqueous solution, slightly unstable in neutral aqueous solution

(16) Property of the substance: Amphoteric substance (dihydrochloride is neutral).

(ii) TAN-547B.dihydrochloride (1) Appearance: White powder.

(2) Specific rotation: $[\alpha]_D^{25}+54.8°\pm15°$ (c=0.56, in water).

(3) Molecular weight: SIMS method, (M+H)+759.

(4) Molecular formula: $C_{29}H_{46}N_{10}O_{12}S.2HCl.(3H_2O)$.

| (5) Elemental analysis (%): | Found*1 | Calcd.*2 |
|---|---|---|
| | C, 39.02 ± 2.0 | C, 39.32 |
| | H, 6.51 ± 1.0 | H, 6.14 |
| | N, 15.46 ± 1.5 | N, 15.81 |
| | | O, 27.09 |
| | S, 3.50 ± 1.0 | S, 3.62 |
| | Cl, 8.27 ± 1.5 | Cl, 8.01 |

*1,*2the same conditions as those of A.

(6) UV spectrum: FIG. 3 $\lambda_{max}^{H2O} 260\pm2$nm $(E_{1cm}^{1\%}=113\pm20)$.

(7) CD spectrum: $[\theta]_{228\pm2}^{H2O}-33600\pm5000$ and $[\theta]_{260\pm2}^{H2O}+30700\pm5000$.

(8) IR spectrum: Main wave numbers (cm$^{-1}$) are shown below: FIG. 4 3370, 3260, 3220, 3080, 3000, 1780, 1735, 1675, 1535, 1460, 1410, 1260, 1170, 1070, 880, 800, 530.

(9) $^{13}$C-NMR spectrum: in D$_2$O, Signals at 100 MHz are shown below (δppm). 179.78(s), 177.92(s), 176.88(s), 176.15(s), 173.49(s), 170.77(s), 166.41(d), 162.25(s), 159.59(s), 134.39(s), 118.69(s), 79.66(s), 72.91(d), 67.11(t), 66.04(d), 56.95(d), 56.03(d), 53.14(d), 51.72(d), 43.61(t), 41.52(t), 37.32(t), 32.62(t), 29.23(t), 28.66(t), 27.50(t), 23.47(t), 19.55(q), 19.51(q).

(10) Amino acid analysis: (the same conditions as that of A) Alanine: 2.1 mole. α-amino-adipic acid: 1.1 mole.

(11) TLC: (the same conditions as that of A) Rf=0.55.

(2) HPLC: (the same conditions as that of A) Rt=6.8(min).

(iii) TAN-547C.dihydrochloride (1) Appearance: White powder.

(2) Specific rotation: $[\alpha]_D^{25}+25.1°\pm15°$ (c=0.49 in water).

(3) Molecular weight: SIMS method; (M+H)+830.

(4) Molecular formula: $C_{32}H_{51}N_{11}O_{13}S.2HCl.(3H_2O)$.

| (5) Elemental analysis (%): | Found*1 | Calcd.*2 |
|---|---|---|
| | C, 39.61 ± 2.0 | C, 40.17 |
| | H, 6.54 ± 1.0 | H, 6.22 |
| | N, 15.92 ± 1.5 | N, 16.10 |
| | | O, 26.75 |
| | S, 3.41 ± 1.0 | S, 3.35 |
| | Cl, 6.41 ± 1.5 | Cl, 7.41 |

*1,*2the same conditions as those of A.

(6) UV spectrum: FIG. 5 $\lambda_{max}^{H2O} 260\pm2$nm $(E_{1cm}^{1\%}=106\pm20)$.

(7) CD spectrum: $[74]_{228\pm2}^{H2O}-34700\pm5000$ and $[\theta]_{260\pm2}^{H2O}+28400\pm5000$.

(8) IR spectrum: the main wave number (cm$^{-1}$) in KBr are as follows. FIG. 6. 3350, 3250, 3070, 3000, 2950, 1780, 1735, 1665, 1530, 1450, 1400, 1300, 1250, 1160, 1060, 790, 520.

(9) $^{13}$C-NMR spectrum: in D$_2$O, Signals at 100 MHz are shown below (δppm). 179.79(s), 178.04(s), 177.47(s), 177.38(s), 176.12(s), 173.47(s), 171.08(s), 166.32(d), 162.07(s), 159.52(s), 135.00(s), 117.27(s), 79.57(s), 72.86(d), 67.10(t), 65.88(d), 57.28(d), 55.87(d), 53.07(d), 52.35(d), 51.62(d), 43.52(t), 41.52(t), 37.27(t), 32.73(t), 29.25(t), 28.48(t), 27.36(t), 23.41(t), 19.45(q), 19.42(q), 19.25(q).

(10) Amino acid analysis: (the same conditions as that of A) Alanine: 3.1 mole. α-amino-adipic acid: 1.1 mole.

(11) TLC: (the same conditions as that of A) Rf=0.60.

(12) HPLC: (the same conditions as that of A) Rt=11.7(min.).

(iv) TAN-547D hydrochloride (1) Appearance: White powder (2) Specific rotation: $[\alpha]_D^{25}+53.5°\pm10°$ (c=0.51, in water).

(3) Molecular weight: SIMS method, (M+H)+645.

(4) Molecular formula: $C_{25}H_{40}N_8O_{10}S.HCl.(3H_2O)$.

| (5) Elemental analysis (%): | Found*1 | Calcd.*2 |
|---|---|---|
| | C, 40.30 ± 2.0 | C, 40.84 |
| | H, 6.44 ± 1.0 | H, 6.44 |
| | N, 15.34 ± 1.5 | N, 15.24 |
| | | O, 28.29 |
| | S, 4.39 ± 1.0 | S, 4.36 |
| | Cl, 4.66 ± 1.5 | Cl, 4.82 |

*1the sample was dried over diphosphorus pentoxide for 15 hours at room temperature under reduced pressure.
*2the value is calculated as the sample contains 3 moles of water.

(6) Ultraviolet absorption (UV) spectrum: FIG. 7. $\lambda_{max}^{H2O} 260\pm2$nm $(E_{1cm}^{1\%}=122\pm20)$.

(7) Circular dichromatic spectrum (CD) spectrum: $[\theta]_{226\pm2}^{H2O}-33000\pm5000$ and $[\theta]_{258\pm2}^{H2O}\pm21000\pm5000$ (−: negative (−) Cotton effect; +: positive (+) Cotton effect).

(8) Infrared absorption spectrum: Main wave number (cm$^{-1}$) in KBr tablet. FIG. 8 3400, 3250, 3075, 2950, 1765, 1735, 1665, 1540, 1450, 1400, 1350, 1270, 1160, 1115, 1065, 1030, 980, 750, 540.

(9) Nucleic magnetic resonance ($^{13}$C-NMR) spectrum: in D$_2$O, signals at 100 MHz are shown below (δppm): 179.52(s), 177.43(s), 176.05(s), 173.72(s), 171.61(s), 167.89(s), 159.57(s), 134.40(s), 118.99(s), 72.64(d), 67.23(t), 61.99(d), 60.13(d), 57.32(d), 56.28(d), 51.97(d), 43.53(t), 41.18(t), 37.58(t), 32.75(t), 28.94(t), 28.43(t), 27.46(t), 23.85(t), 19.70(q).

(10) Amino acid analysis: in 5.5N—HCl, 110° C., the sample was hydrolized for 15 hours. Alanine: about 1 mole. α-Amino-adipic acid: about 1 mole.

(11) Thin layer chromatography (TLC): spot film, cellulose (Tokyo Chemical Industries, Ltd.) Solvent system, acetonitrile: 3% ammonium sulfate (1:1), Rf=0.50.

(12) High performance liquid chromatography (HPLC): column, YMC pack A312 (Yamamura Chemical Research Institute), mobile phase 5% methanol/0.01M phosphate buffer (pH 3.0), 2 ml/min. Rt=4.2(min).

The following properties are in common among the components D, E and F (as hydrochloride(s)).

(13) Solubility: Easily soluble: water, aqueous acetone, aqueous alcohol. Hardly soluble: dimethylsulfoxide, methanol, acetone, ethyl acetate.

(14) Color reaction: Positive: ninhydrine, Greig-Lieback, Sakaguchi reactions. Negative: Ehrlich, Barton reactions, potassium permanganate.

(15) Stability: Slightly unstable in acidic or neutral aqueous solution. Unstable in basic aqueous solution.

(16) Properties of the substance: Amphoteric substance (dihydrochloride is neutral).

(v) TAN-547E.dihydrochloride
 (1) Appearance: White powder
 (2) Specific rotation: $[\alpha]_D^{25} + 31.1° \pm 10°$ (c=0.51 in water).
 (3) Molecular weight: method, (M+H)+716.
 (4) Molecular formula: $C_{28}H_{45}N_9O_{11}S \cdot 2HCl \cdot (3H_2O)$.

| (5) Elemental analysis (%): | Found*[1] | Calcd.*[2] |
|---|---|---|
| | C, 39.86 ± 2.0 | C, 39.90 |
| | H, 6.28 ± 1.0 | H, 6.34 |
| | N, 14.64 ± 1.5 | N, 14.96 |
| | | O, 26.58 |
| | S, 3.79 ± 1.0 | S, 3.80 |
| | Cl, 7.83 ± 1.5 | Cl, 8.41 |

*[1],*[2]The same conditions as those of D.

(6) UV spectrum: FIG. 9. $\lambda_{max}^{H2O} 260 \pm 2$nm ($E_{1cm}^{1\%} 32\ 114 \pm 20$).

(7) CD spectrum: $[\theta]_{226\pm2}^{H2O} - 31000 \pm 5000$ and $[\theta]_{256\pm2}^{H2O} + 21000 \pm 5000$.

(8) IR spectrum: Main wave number (cm$^{-1}$) are shown below. FIG. 10. 3375, 3260, 3220, 3075, 2950, 1770, 1735, 1660, 1540, 1455, 1400, 1345, 1250, 1160, 1115, 1065, 1035, 980, 880, 815, 540.

(9) $^{13}$C-NMR spectrum: in D₂O, the signals at 100 MHz are shown below (δppm) 179.48(s), 177.82(s), 177.36(s), 176.12(s), 173.46(s), 171.49(s), 167.83(s), 159.54(s), 134.37(s), 118.99(s), 72.84(d), 67.19(t), 61.95(d), 60.10(d), 57.31(d), 55.96(d), 53.04(d), 51.63(d), 43.53(t), 41.47(t), 37.53(t), 32.72(t), 29.14(t), 28.38(t), 27.43(t), 23.81(t), 19.44(q)(two occurrences).

(10) Amino acid analysis: (the same conditions as those of D). Alanine: about 2 moles. α-amino-adipic acid: about 1 mole.

(11) TLD: (the same conditions as those of D) Rf=0.54.

(12) HPLC: (the same conditions as those of D) Rt=4.9(min).

(vi) TAN-547F.dihydrochloride
 (1) Appearance: White powder
 (2) Specific rotation: $[\alpha]_D^{25} + 5.8° \pm 3°$ (c=0.49, in water).
 (3) Molecular weight: SIMS method, (M+H)+787
 (4) Assumed molecular formula: $C_{31}H_{50}N_{10}O_{12}S \cdot 2HCl \cdot (3H_2O)$.

| (5) Elemental analysis (%): | Found*[1] | Calcd.*[2] |
|---|---|---|
| | C, 40.27 ± 2.0 | C, 40.74 |
| | H, 6.52 ± 1.0 | H, 6.40 |
| | N, 14.52 ± 1.5 | N, 15.33 |
| | | O, 26.26 |
| | S, 2.92 ± 1.0 | S, 3.51 |
| | Cl, 7.12 ± 1.5 | Cl, 7.76 |

*[1],*[2]the same conditions as those of D.

(6) UV spectrum: FIG. 11 $\lambda_{max}^{H2O} 260 \pm 2$nm ($E_{1cm}^{1\%} = 94 \pm 20$).

(7) CD spectrum: $[\theta]_{226\pm2}^{H2O} - 30000 \pm 5000$ and $[\theta]_{258\pm2}^{H2O} + 17000 \pm 5000$.

(8) IR spectrum: the main wave number (cm$^{-1}$) in KBr are as follows. FIG. 12 3360, 3250, 3070, 3000, 2950, 1770, 1735, 1660, 1535, 1455, 1395, 1345, 1240, 1160, 1115, 1065, 1030, 980, 960, 870, 510.

(9) $^{13}$C-NMR spectrum: in D₂O, Signals at 100 MHz are shown below (δppm) 179.39(s), 177.87(s), 177.26(s), 176.47(s), 176.15(s), 173.45(s), 170.68(s), 168.00(s), 159.65(s), 133.51(s), 121.03(s), 72.90(d), 67.15(t), 62.04(d), 60.21(d), 56.84(d), 55.91(d), 53.02(d), 52.44(d), 51.77(d), 43.64(t), 41.54(t), 37.47(t), 32.54(t), 29.30(t), 28.56(t), 27.41(t), 23.77(t), 19.55(q), 19.44(q), 19.37(q).

(10) Amino acid analysis: (the same conditions as those of D). Alanine: about 3 moles. α-amino-adipic acid: about 1 mole.

(11) TLC: (the same conditions as those of D) Rf=0.58.

(12) HPLC: (the same conditions as those of D) Rt=6.5 (min).

In said properties, it was determined by HPLC that the alanine and α-amino-adipic acid are L-form and D-form, respectively.

From said physico-chemical properties, it is assumed that the chemical structure of said compounds are those shown by the formula (I).

The biological activity of the compound (I) is mentioned hereinafter.

The antimicrobial spectra of the compound (I) are shown in Table 1.

TABLE 1

| Test organism | Minimal inhibitory concentration (μg/ml)* TAN-547 | | | | | |
|---|---|---|---|---|---|---|
| | A | B | C | D | E | F |
| Escherichia coli NIHJ JC-2 | 25 | 25 | 25 | 50 | 50 | >100 |
| Pseudomonas aeruginosa IFO 3080 | >50 | >50 | >50 | >100 | >100 | >100 |
| Serratia marcescens IFO 12648 | 50 | 50 | 50 | >100 | >100 | >100 |
| Alcaligenes faecalis IFO 13111 | 6.25 | 6.25 | 12.5 | 12.5 | 12.5 | 12.5 |
| Proteus vulgalis IFO 3988 | 50 | 25 | 50 | 50 | 50 | 100 |
| Salmonella typhimurium IFO 12529 | 50 | 25 | 25 | 50 | 50 | 100 |
| Klebsiella pneumoniae IFO 3317 | 50 | 50 | 50 | 100 | 100 | 100 |
| Citrobacter freundii IFO 12681 | 50 | 50 | 50 | >100 | >100 | >100 |
| Acinetobacter calcoaceticus IFO 12552 | 1.56 | 3.13 | 6.25 | 50 | 100 | 100 |
| Staphylococcus aureus | >50 | >50 | >50 | 25 | 25 | 12.5 |

TABLE 1-continued

| Test organism | Minimal inhibitory concentration (μg/ml)* TAN-547 | | | | | |
|---|---|---|---|---|---|---|
| | A | B | C | D | E | F |
| FDA 209P | | | | | | |
| Bacillus subtilis NIHJ PCI219 | 12.5 | 12.5 | 12.5 | 0.78 | 1.56 | 1.56 |
| Bacillus megaterium IFO 12108 | 12.5 | 12.5 | 12.5 | 0.78 | 1.56 | 1.56 |
| Brevibacterium thiogenitalis ATCC 19240 | 6.25 | 6.25 | 12.5 | 1.56 | 3.13 | 3.13 |

(Note):
*Culture medium: 17.5 g of Bacto antibiotic medium 3 (Difco), 5 g of Bacto yeast extract (Difco), 20 g of Bacto agar (Difco), 1 l of distilled water; pH 7.0
The amount of inoculated microorganism: 1 loopful of about $10^6$/ml of microorganism suspension.

The therapeutic effect of TAN-547 to infectious disease of mice is shown in Table 2.

TABLE 2

| Infectious microorganism | TAN-547 hydrochloride(s) | Administration route | $ED_{50}$ mg/kg |
|---|---|---|---|
| Escherichia coli 0-111 | A | subcutaneous (SC) | 18.2 |
| | B | SC | 17.2 |
| | C | SC | 16.2 |
| | D | SC | 9.92 |
| | E | SC | 21.0 |
| | F | SC | 25.0 |

The stability of TAN-547 A, B or C to β-lactamase is shown in Table 3. As seen from the Table 3, TAN-547A, B or C is remarkably stable to β-lactamase.

TABLE 3

| β-lactamase | Relative ratio of hydrolysis rate | | | | | |
|---|---|---|---|---|---|---|
| | TAN-547 | | | | | |
| | A | B | C | CPZ | CER | PCG |
| β-lactamase produced by Escherichia coli TN 713 | <0.01 | <0.01 | <0.01 | 11.2 | 21 | 100 |
| β-lactamase produced by Klebsiella oxytoca TN 1719 | <0.01 | <0.01 | <0.01 | 1.55 | 30 | 100 |
| β-lactamase produced by Serratia marcescens TN 81 | <0.01 | <0.01 | <0.01 | 11.6 | 100 | 12 |
| β-lactamase produced by Proteus vulgalis GN 4413 | <0.01 | <0.01 | <0.01 | 10.5 | 100 | 16 |

CPZ: cefoperazone,
CER: cephaloridine,
PCG: benzylpenicillin

In the above Table 3, the stabilities against the β-lactamase produced by Escherichia coli TN 713 and β-lactamase produced by Klebsiella oxytoca TN 1719 are expressed on a numerical scale, whereby the stabilities of PCG against these are rated at 100. Also, the stabilities against the β-lactamase produced by Serratia marcescens and β-lactamase produced by Proteus vulgaris are expressed on a numerical scale, whereby the stabilities of CER against these are rated at 100.

When Antibiotic TAN-547 C.dihydrochloride or TAN-547 D.hydrochloride was administered subcutaneously in amount of 1 g/kg to mice, no death was observed, and consequently, the compound (I) is considered to be low-toxic.

As is evident from these data, the compound (I) exhibits antimicrobial activity against gram-positive and negative bacteria including β-lactamase producing strains, and is an antibiotic with low toxicity to mammals, etc. Therefore, the compound (I) can be used in the treatment of infectious disease caused by bacteria in mammals (e.g., mouse, rat, rabbit, dog, human being, etc.).

In order to use the compound (I) for example as a therapeutic agent against infectious disease caused by bacteria, the compound (I) is administered, for example as an injection by a route other than oral route, to the above mammals subcutaneously or intramuscularly in the dose of about 1 to 50 mg/kg/day, preferably about 5 to 20 mg/kg/day. As preparations for oral administration, the compound (I) is formulated into capsules, which are administered in the dose of about 1 to 100 mg/kg/day as the compound (I), preferably about 5 to 50 mg/kg/day.

In addition, the compound (I) can be used as a bactericide. The compound (I), for example, is made into a liquid preparation having the compound (I) in concentration of about 0.01 to 0.1 W/V % dissolved in distilled water, and an ointment containing about 0.2 to 20 mg, preferably about 1 to 10 mg of the compound (I) per gram of the preparation, and they can be applied for sterilization and disinfection of hands, feet, eyes, ears, etc. of the above mammals by coating to these parts.

Based on the above-mentioned characteristics, the compound (I) is considered to be a novel compound.

As mentioned above, as the present compound (I) is stable to cephalosporinase, the present compound (I) is useful as a medicine.

Furthermore, by the present process employing a bacteria, the objective compound (I) can be produced in a shorter time.

BRIEF DESCRIPTION OF THE DRAWINGS

FIG. 1, FIG. 3, FIG. 5, FIG. 7, FIG. 9 and FIG. 11 show the ultraviolet absorption spectra of Antibiotic TAN-547 A.dihydrochloride, B.dihydrochloride, C.dihydrochloride, D.hydrochloride, E.dihydrochloride and F.dihydrochloride, respectively, while

Figure 1:
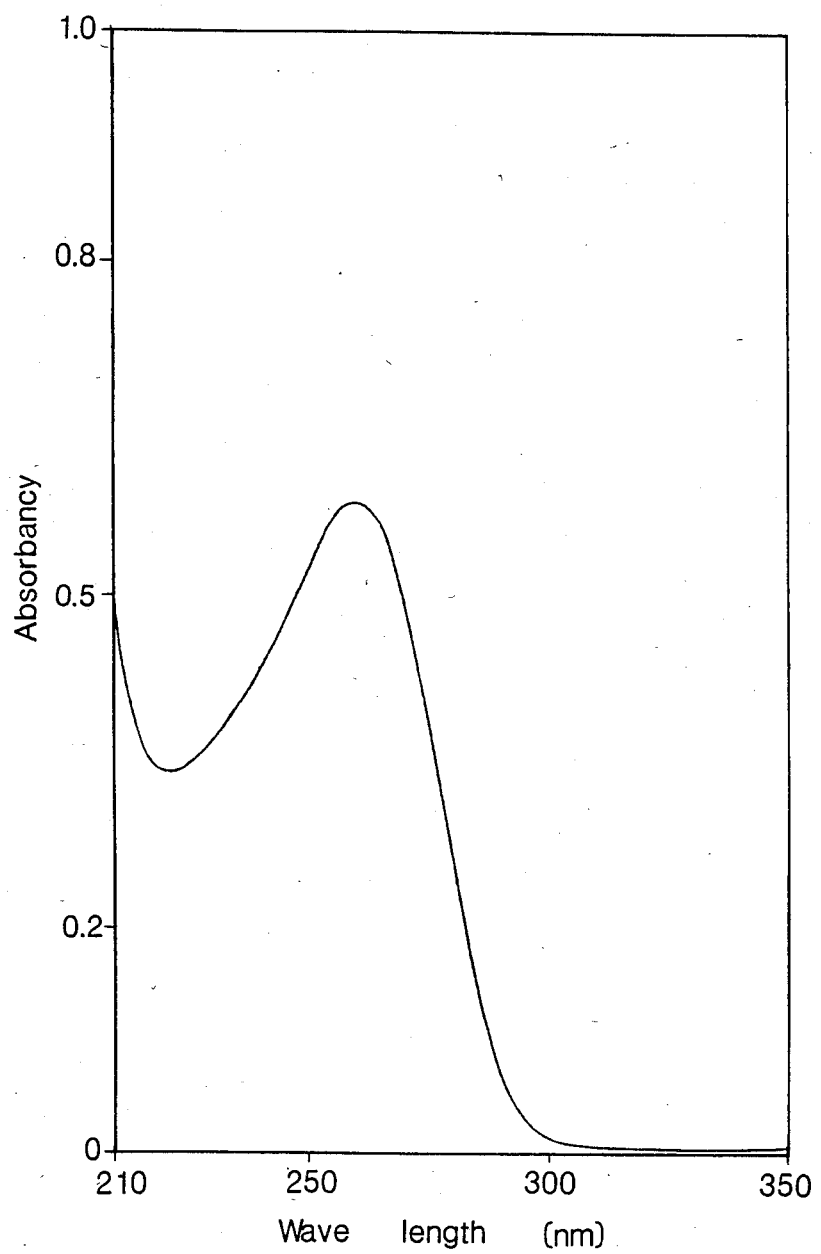
Figure 2:
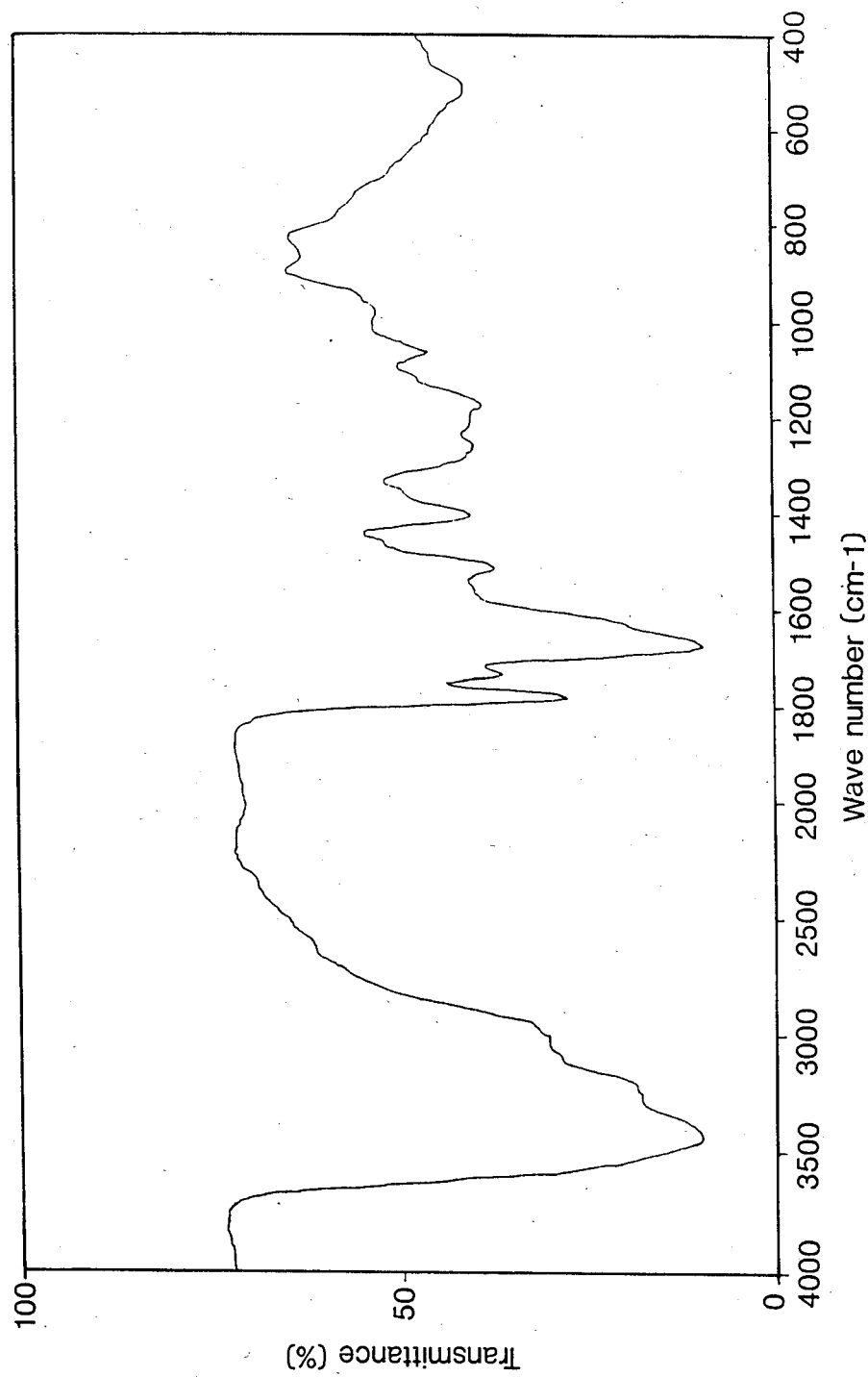
FIG. 2, FIG. 4, FIG. 6, FIG. 8, FIG. 10 and FIG. 12 show the infrared absorption spectra of Antibiotic TAN-547 A.dihydrochloride, B.dihydrochloride and C.dihydrochloride, D.hydrochloride, E.dihydrochloride and F.hydrochloride, respectively.
Figure 3:
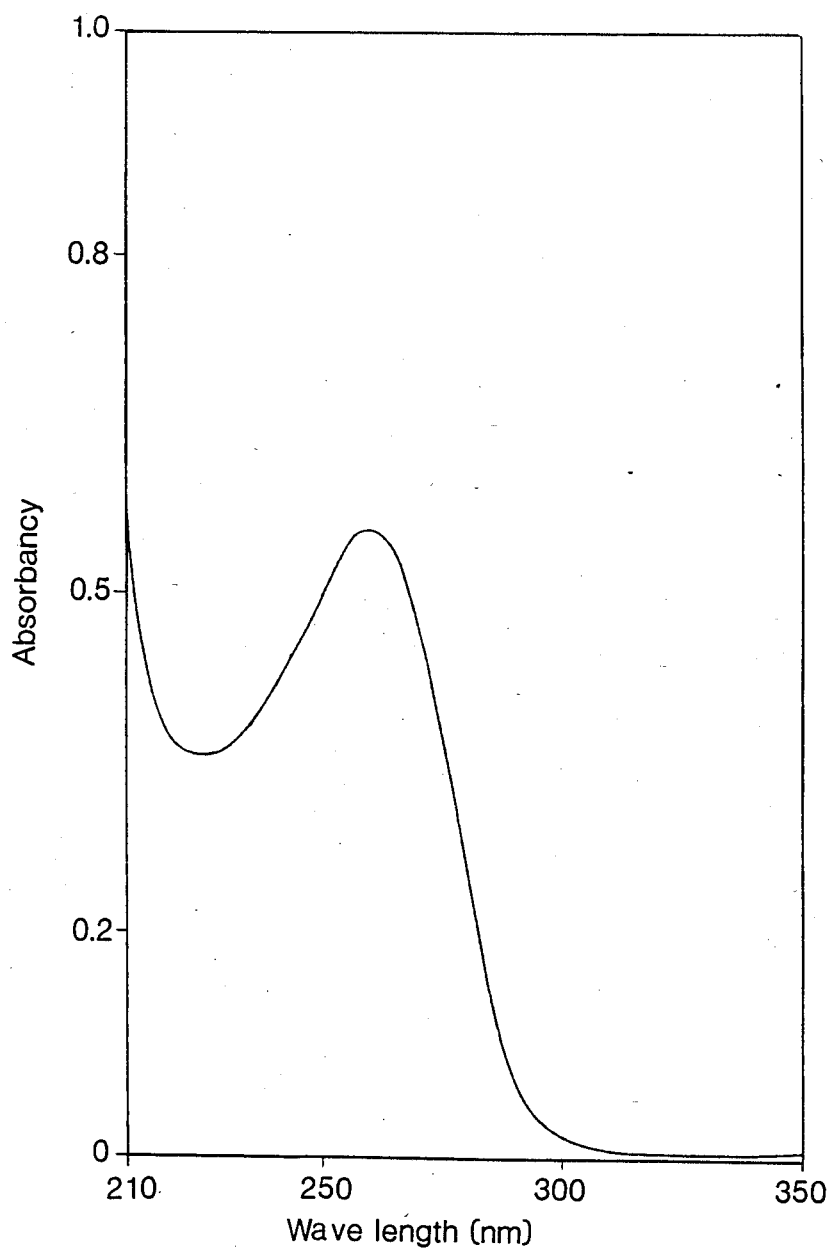
Figure 4:
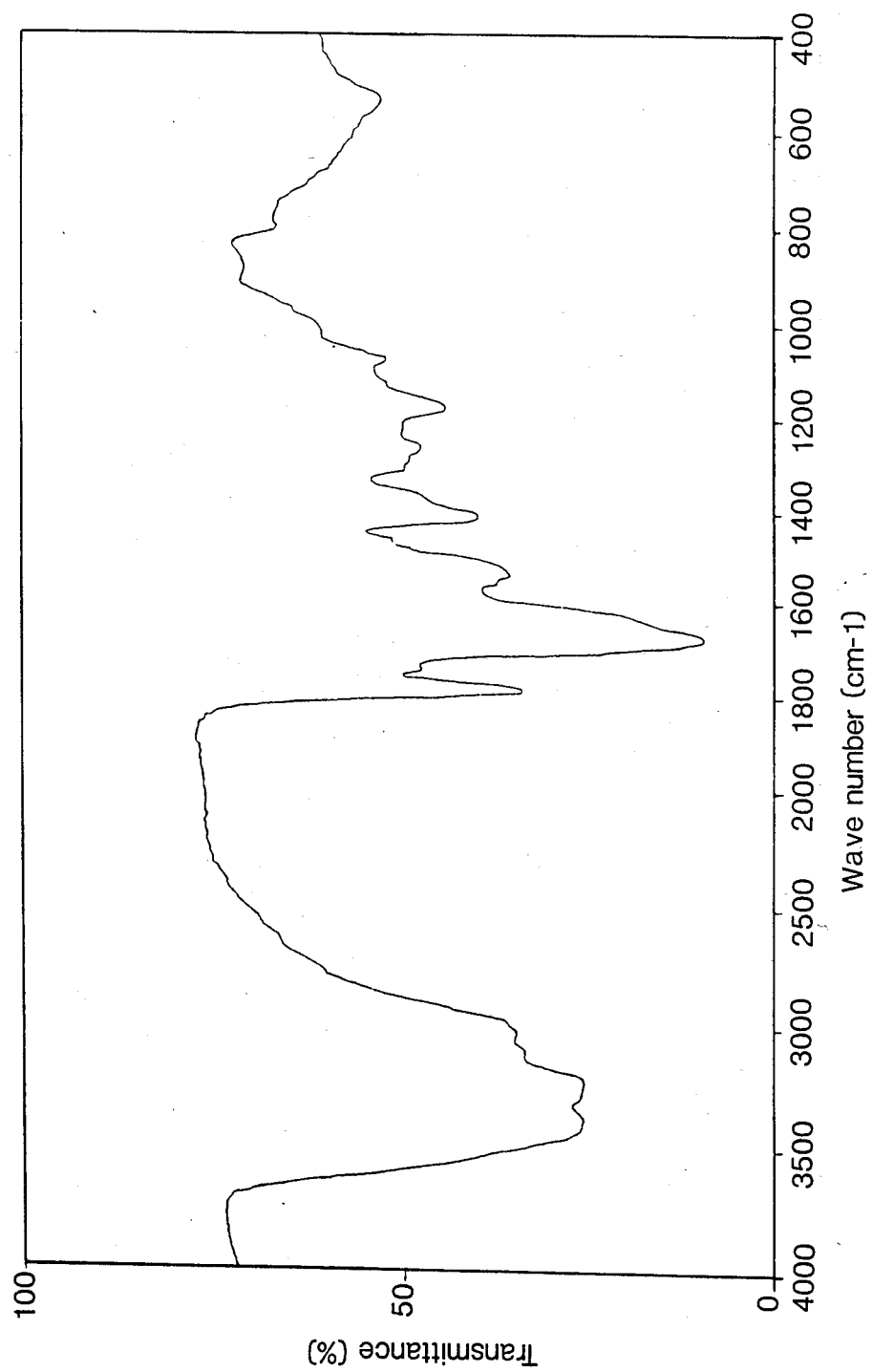
Figure 5:
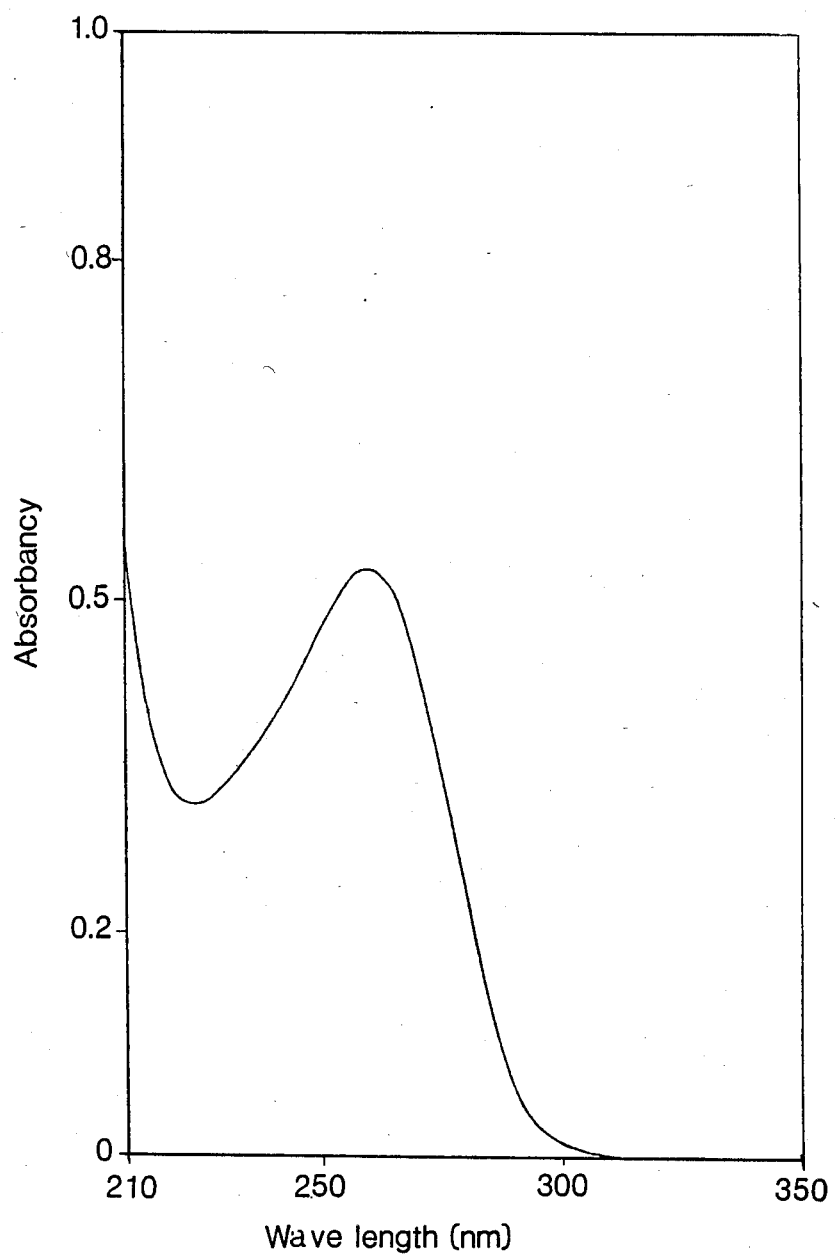
Figure 6:
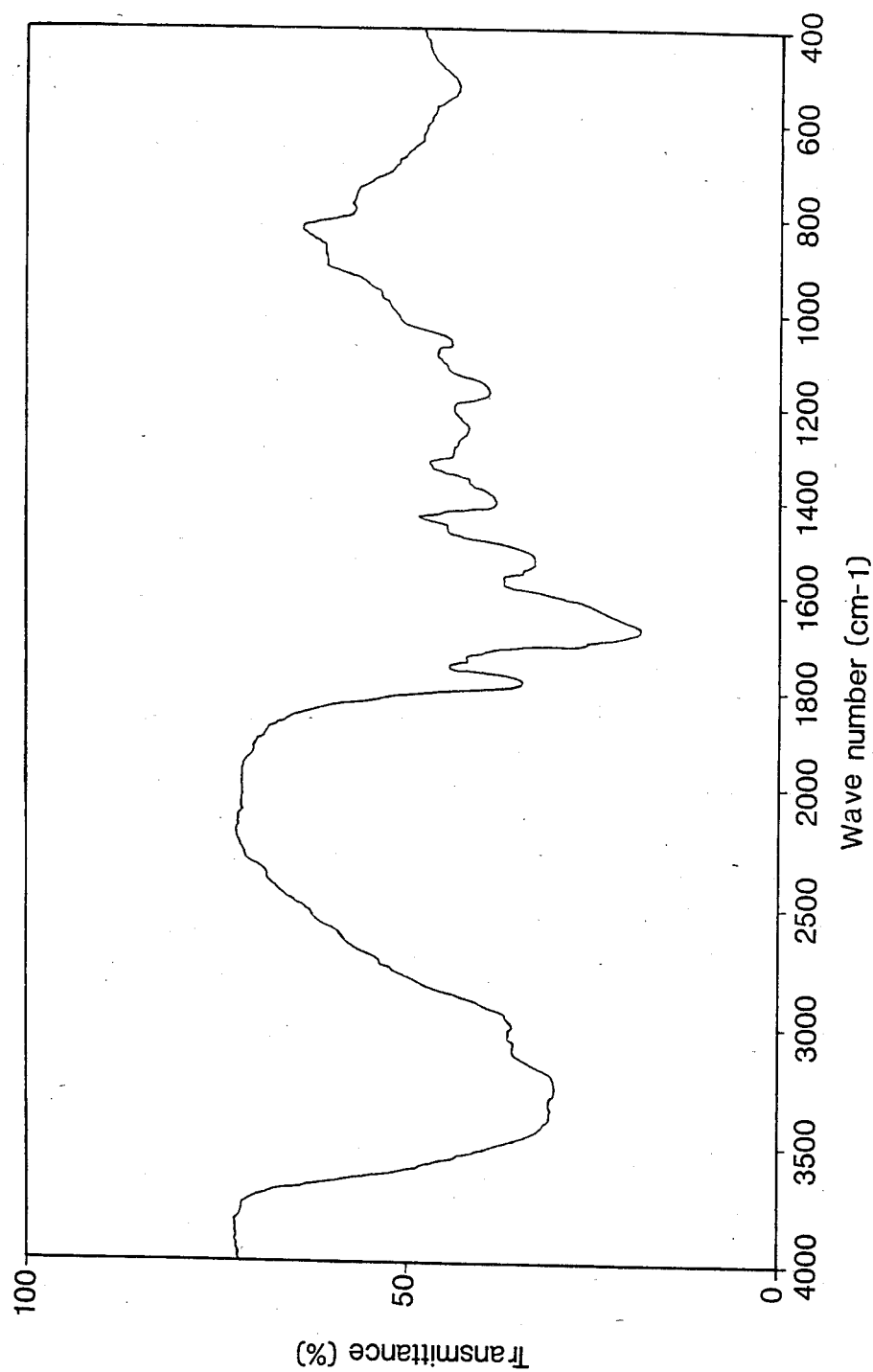
Figure 7:
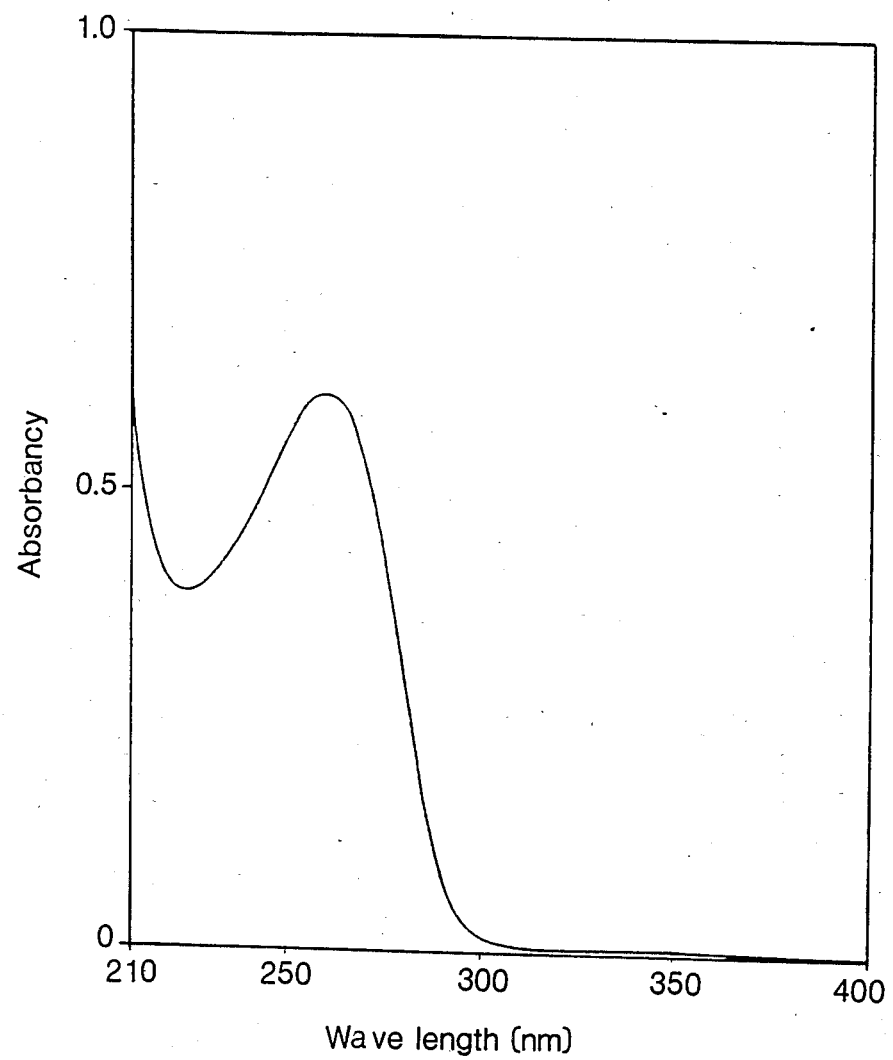
Figure 8:
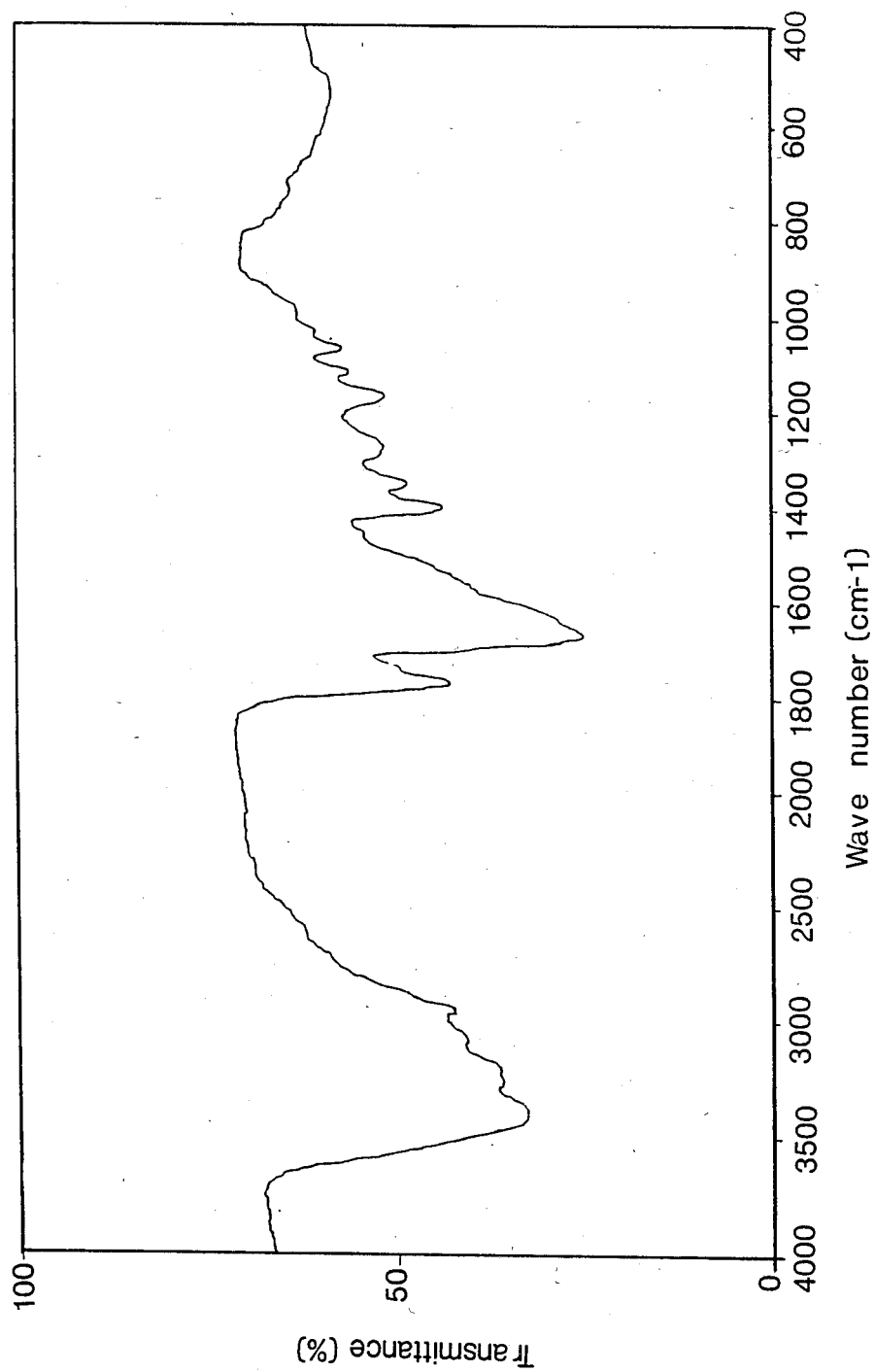
Figure 9:
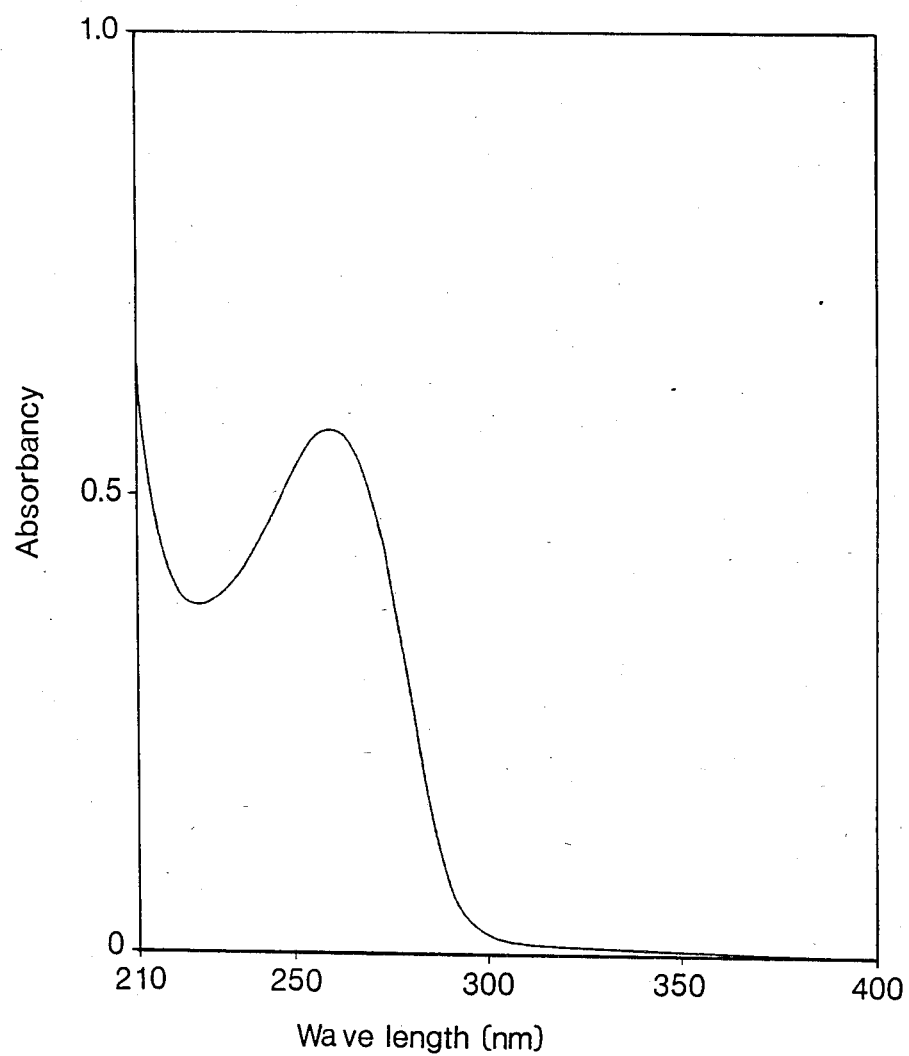
Figure 10:
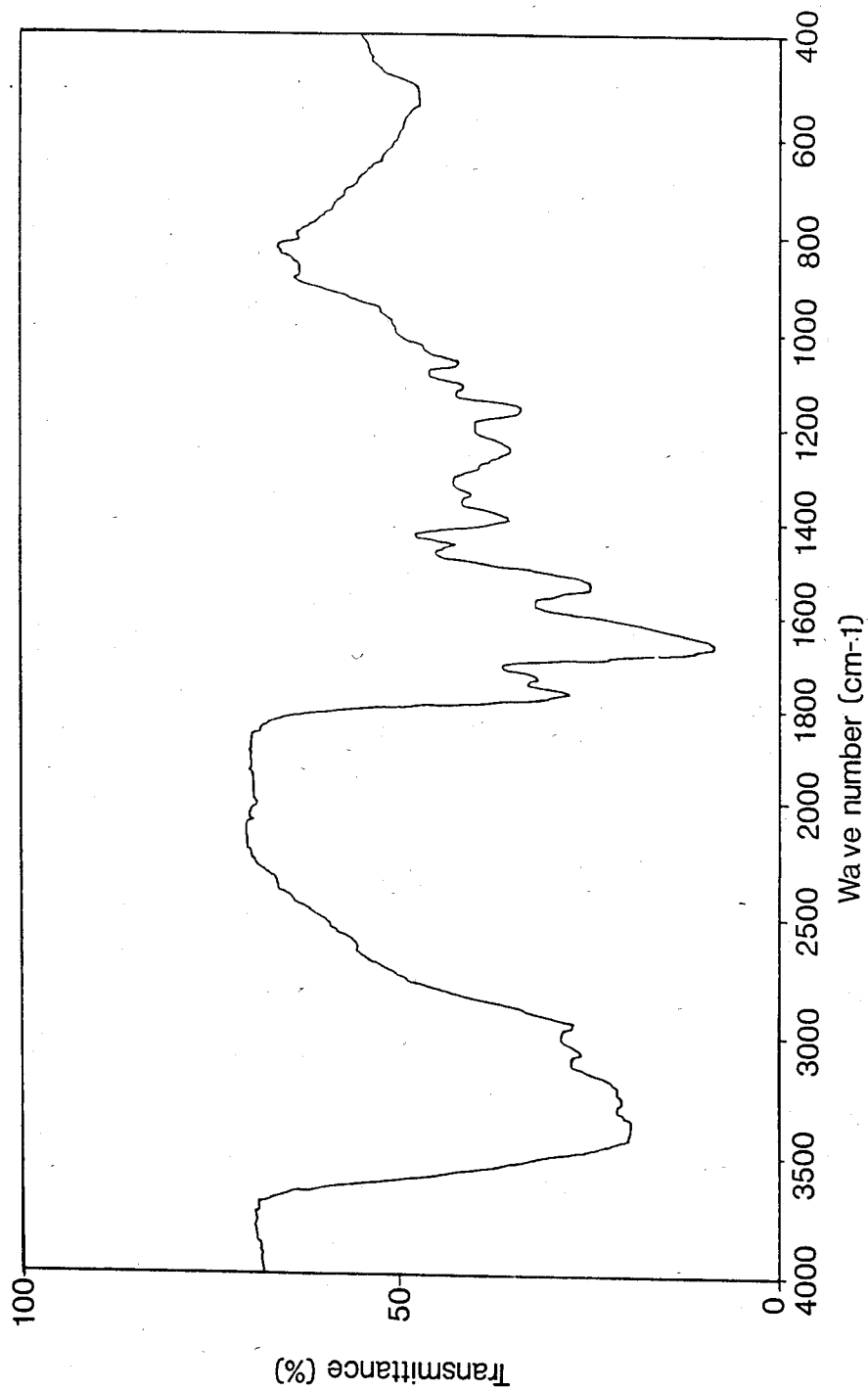
Figure 11:
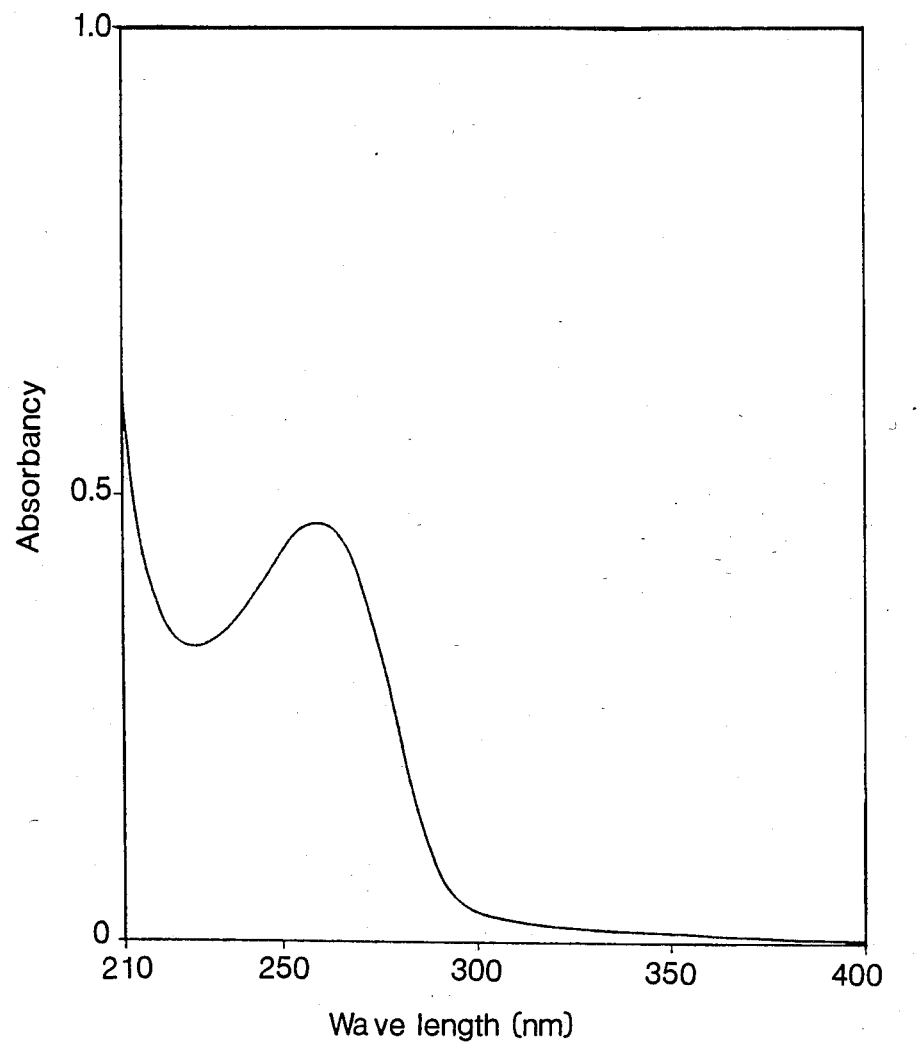
Figure 12:
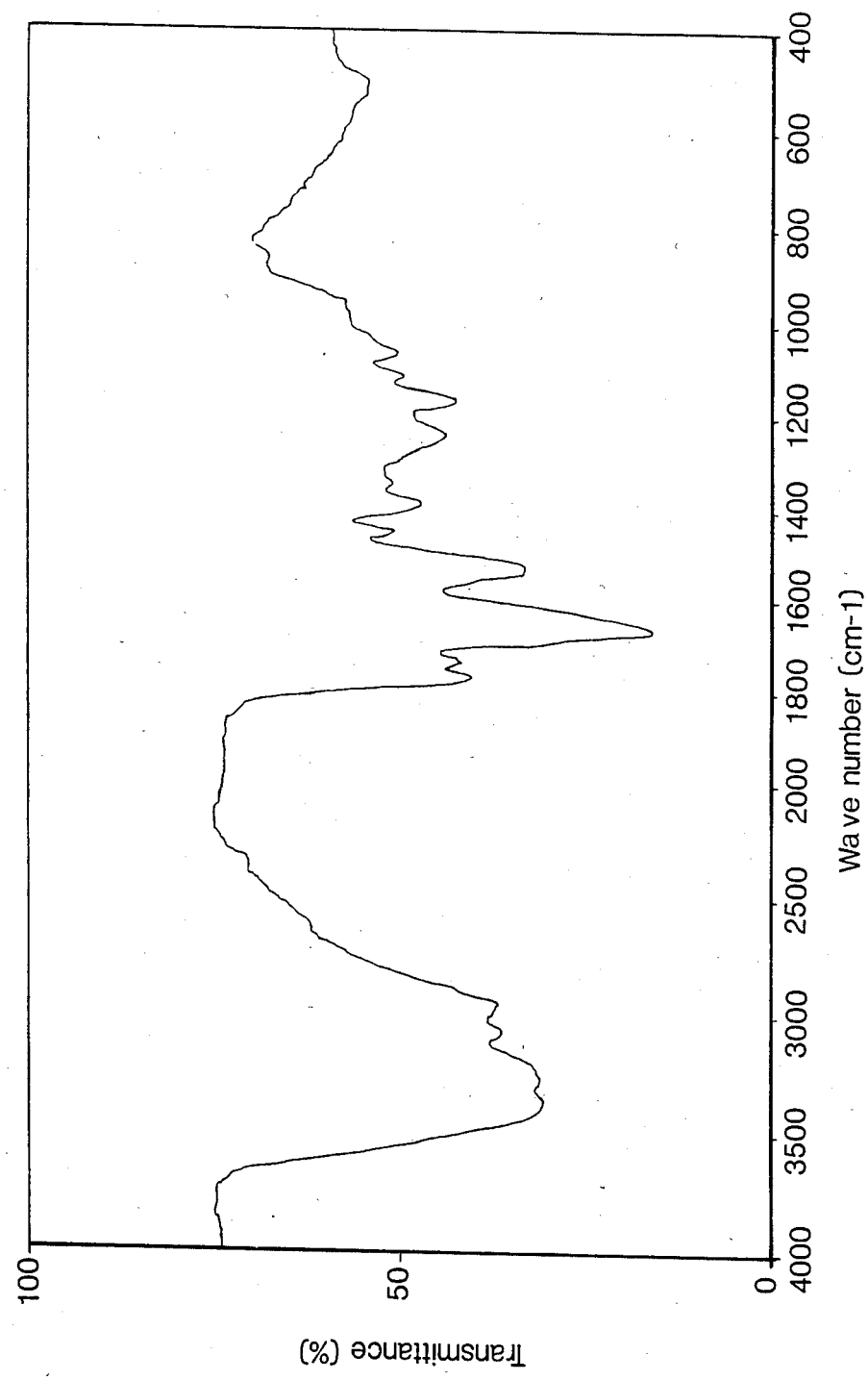

The examples are described in the following to illustrate the present invention more in detail. The term % means a weight/volume %, unless otherwise noted.

EXAMPLE 1

Lysobacter lactamgenus YK-90 (IFO 14288, FERM BP-575) grown on a nutrient agar slant was used to inoculate three 200-ml Erlenmeyer flasks each containing 40 ml of a culture medium of an aqueous solution (pH 7) composed of 2% of glucose, 3% of soluble starch, 1% of raw soybean flour, 1% of corn steep liquor, 0.5% of Polypepton (produced by Daigo Nutritive Chemicals, Ltd., Japan) and 0.3% of sodium chloride and 0.5% of precipitating calcium carbonate admixed, and shake culture was carried out on a rotary shaker at 24° C. for 48 hours to obtain seed cultures.

Then, 4000 ml of a culture medium consisting of an aqueous solution (pH 6.5) containing 3% of dextrin, 1.5% of raw soybean flour, 1.5% of corn gluten meal, 0.2% of Polypepton and 0.1% of sodium thiosulfate and 0.5% of precipitating calcium carbonate admixed were distributed in 40-ml portions into 200-ml Erlenmeyer flasks, which were then sterilized at 120° C. for 20 minutes. A 1-ml portion of the seed culture was transferred to each of these 200-ml Erlenmeyer flasks containing the said culture medium, and incubated on a rotary shaker at 24° C. for 72 hours under the conditions of 200 r.p.m.

The culture broth (20 l) obtained by the above procedure was adjusted to pH 3.5 with 7% oxalic acid, admixed with Hyflo-Supercel (Johns Manville Product, U.S.A.) and filtered to obtain a filtrate (16 l). The filtrate was adjusted to pH 6.8, and passed through a column packed with activated carbon (1 l). The column was washed with water (3 l), and Antibiotic TAN-547 was eluted with 8% isobutanol-N/200 hydrochloric acid (8 l). The eluate was concentrated to 1.8 l, and the concentrate was passed through a column of Amberlite CG-50 (H+type, 1.4 l) (produced by Rohm & Haas Co., U.S.A.). The column was washed with water (4.5 l), and the elution was conducted with N/100 hydrochloric acid (9 l) by fractionation. The active fractions were collected and concentrated, and the concentrate was adjusted to pH 7.3 and passed through a column packed with Diaion HP-20 (50 to 100 mesh, 0.5 l) (produced by Mitsubishi Chemical Industries, Ltd., Japan). After the column was washed with 0.01M phosphate buffer (pH 7.3, 1.5 l), elution was conducted with 0.01M phosphate buffer (pH 3.5, 5 l) by fractionation. The active fractions were collected, and the eluate was adjusted to pH 7.2 and passed through a column packed with activated carbon (100 ml). The column was washed with water (300 ml), and elution was carried out with 8% isobutanol-N/200 hydrochloric acid (600 ml). The eluate was concentrated, and the concentrate was passed through a column packed with CM-Sephadex C 25 (Na+ type, 200 ml)(produced by Pharmacia Fine Chemicals Co., Sweden), followed by elution with 0.02M aqueous sodium chloride solution (6 l). Individual fractions were subjected to analysis by HPLC, and the fractions containing TAN-547 A, B and C as a principal component, respectively, were collected.

The fraction containing TAN-547 A as a principal component was adjusted to pH 7.2, and passed through a column packed with activated carbon (10 ml), and after the column was washed with water (30 ml), elution was carried out with 8% isobutanol-N/200 hydrochloric acid (70 ml). The eluate was concentrated, and the concentrate was lyophilized to give a crude powder (61 mg) of TAN-547 A.dihydrochloride.

By conducting the same procedure with the fractions containing TAN-547 B and C as a principal component, respectively, there were obtained a crude powder (144 mg) of TAN-547 B.dihydrochloride and a crude powder (226 mg) of TAN-547 C.dihydrochloride.

The crude powder (61 mg) of TAN-547 A.dihydrochloride was subjected to preparative HPLC for separation with YMC-GEL ODS I-15(produced by Yamamura Chemical Research Institute, Japan) used as a support, and elution fractionation was carried out with 0.02M phosphate buffer (pH 3.0). The individual fractions were subjected to analysis by HPLC, and the fractions showing a single peak were collected. The active fraction was adjusted to pH 7.5 with 1N NaOH, readjusted to pH 3.0 with 1N HCl, and passed through a column packed with activated carbon (5 ml). After the column was washed with water (25 ml), elution was conducted with 8% aqueous isobutanol (25 ml). The eluate was concentrated and lyophilized to give a white powder (40 mg) of TAN-547 A.dihydrochloride.

Crude powders of TAN-547 B and C.dihydrochlorides were also subjected to preparative HPLC for separation in the same manner to yield a white powder (96 mg) of TAN-547 B.dihydrochloride and a white powder (112 mg) of TAN-547 C.dihydrochloride.

EXAMPLE 2

*Lysobacter lactamgenus* YK-90 (IFO 14288, FERM BP-575) grown on a nitrient agar slant was used to inoculate two 2-l Sakaguchi flasks each containing 500 ml of a culture medium consisting of an aqueous solution (pH 7.0) having the composition of 2% of glucose, 3% of soluble starch, 1% of raw soybean flour, 1% of corn steep liquor, 0.5% of Polypepton and 0.3% of sodium chloride admixed with 0.5% of precipitating calcium carbonate, and incubated on a reciprocating shaker at 24° C. for 48 hours. The total volume of the resulting culture broth was transferred to a tank of a 200-l capacity containing 120 l of the above-described culture medium being admixed with 0.05% of an antifoam, Actcol (produced by Takeda Chemical Industries, Ltd., Japan), and incubation was carried out at 24° C. for 48 hours with aeration at the rate of 120 l/min. and agitation at 150 r.p.m. The total volume of the resulting culture broth was transferred to a tank of a 6000-l capacity containing 4000 l of a culture medium consisting of an aqueous solution (pH 6.5) having the composition of 3% of dextrin, 1.5% of raw soybean flour, 1.5% of corn gluten meal, 0.2% of Polypepton and 0.1% of sodium thiosulfate admixed with 0.5% of precipitating calcium carbonate and 0.05% of Actcol, and incubation was carried out at 24° C. for 66 hours with aeration at the rate of 4000 l/min and agitation at 120 r.p.m.

The culture (3900 l) obtained by the above procedure was adjusted to pH 6.1 with 2N hydrochloric acid, admixed with Hyflo-Supercel, filtered and washed with water to give a filtrate (4370 l). The filtrate was adusted to pH 7.0 and passed through a column packed with Dowex-50W (Na+ type, 50 to 100 mesh, 120 l). The column was washed with water (360 l), and elution was carried out with 2M aqueous sodium chloride solution (1800 l). The eluate was passed through a column of activated carbon (60 l), and after the column was washed with water (180 l), elution was carried out with 8% isobutanol-N/200 hydrochloric acid (420 l). The eluate was concentrated to 40 l, and the concentrate was adjusted to pH 7.3 and passed through a column packed with Diaion HP-20 (40 l). The column was washed with 0.01M phosphate buffer (pH 7.3, 80 l), and elution was carried out with 0.01M phosphate buffer (pH 3.5, 400 l).

The eluate was passed through a column of activated carbon (10 l), and after the column was washed with water (30 l), elution was carried out with 8% isobutanol-N/200 hydrochloric acid (70 l). The eluate was concentrated to 2 l, and the concentrate was adjusted to pH 7.3 and passed through a column packed with Diaion HP-20 (50 to 100 mesh, 4 l). The column was washed with 0.01M phosphate buffer (pH 7.3, 12 l), elution was carried out with 0.01M phosphate buffer (pH 3.5, 40 l). Individual fractions were subjected to analysis by HPLC and separated into two groups, fractions containing TAN-547 A, B and C as a principal component and fractions containing TAN-547 D, E and F as a principal component. The fractions containing TAN-547 D, E and F were collected and passed through a column of activated carbon (300 ml), and after the column was washed with water, elution was carried out 8% isobutanol-N/200 hydrochloric acid (2100 ml). After the eluate was concentrated, the concentrate was passed through a column packed with CM-Sephadex C 25 (Na+ type, 300 ml), and elution was carried out with 0.02M aqueous sodium chloride solution (12 l). Individual fractions were subjected to analysis by HPLC, and fractions containing TAN-547 D, E and F as a principal component, respectively, were collected.

The fractions containing TAN-547 F as a principal component were collected and passed through a column of activated carbon (50 ml), and the column was washed with water (150 ml), followed by elution with 8% isobutanol-N/200 hydrochloric acid (350 ml). The eluate was concentrated and the concentrate was lyophilized to give a crude powder (1.0 g) of TAN-547 F. The same procedure were conducted with the fractions containing TAN-547 D and E as a principal component, respectively, and there were obtained a crude powder (0.3 g) of TAN-547 D and a crude powder (0.6 g) of TAN-547 E.

The crude powder (1.0 g) of TAN-547 F was subjected to preparative HPLC for separation using YMC-GEL ODS 30/60 (produced by Yamamura Chemical Research Institute of Japan) as a support, and elution fractionation was carried out with 2% methanol-0.02M phosphate buffer (pH 3.0). Individual fractions were subjected to analysis by HPLC, and fractions containing TAN-547 F as a principal component were collected, adjusted to pH 7.1 and passed through a column of activated carbon (20 ml). After the column was washed with water (60 ml), elution was carried out with 8% isobutanol-N/200 hydrochloric acid (140 ml), and the eluate was concentrated. The concentrate was subjected to preparative HPLC for separation using TSK-GEL, LS-410 (produced by Toyo Soda Manufacturing Co. Ltd., Japan) as a support, and elution fractionation was carried out with 1% methanol-0.01M phosphate buffer (pH 3.0). Individual fractions were subjected to analysis by HPLC and fractions showing a single peak were collected. The effective fractions were adjusted to pH 7.0 with 1N NaOH, readjusted to pH 3.0 with 1N HCl and passed through a column packed with activated carbon (10 ml), and after the column was washed with water (50 ml), elution was carried out with 8% aqueous isobutanol solution. The eluate was concentrated, and the concentrate was lyophilized to give a white powder (69 mg) of TAN-547 F dihydrochloride. The crude powders of TAN-547 D and E were also subjected to preparative HPLC for separation in the same manner, and there were obtained a white powder (30 mg) of TAN-547 D monohydrochloride and a white powder (63 mg) of TAN-547 E dihydrochloride.

What we claim is:

1. A compound of the formula:

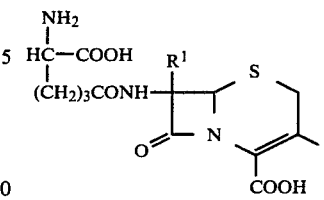

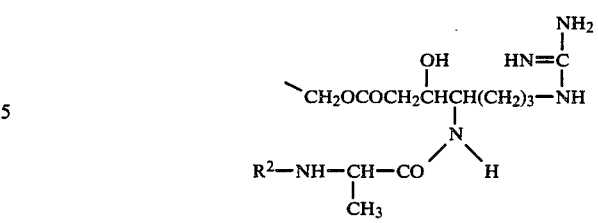

wherein $R^1$ stands for hydrogen or formylamino, $R^2$ stands for hydrogen, alanyl or alanyl-alanyl, or its salt.

2. A compound as claimed in claim 1, wherein $R^1$ is hydrogen.

3. A compound as claimed in claim 1, wherein $R^1$ is formylamino.

4. A compound as claimed in claim 1, wherein $R^1$ is formylamino and $R^2$ is hydrogen or alanyl.

5. A compound as claimed in claim 1, wherein $R^1$ is formylamino and $R^2$ is alanyl-alanyl.

6. A compound as claimed in claim 1, wherein $R^1$ is hydrogen and $R^2$ is hydrogen.

7. A compound as claimed in claim 1, wherein $R^1$ is hydrogen and $R^2$ is alanyl.

8. A compound as claimed in claim 1, wherein $R^1$ is hydrogen and $R^2$ is alanyl-alanyl.

* * * * *